United States Patent [19]

Fletcher et al.

[11] 4,061,561
[45] Dec. 6, 1977

[54] AUTOMATIC MULTIPLE-SAMPLE APPLICATOR AND ELECTROPHORESIS APPARATUS

[76] Inventors: James C. Fletcher, Administrator of the National Aeronautics and Space Administration, with respect to an invention of; Benjamin W. Grunbaum, Moraga, Calif.

[21] Appl. No.: 744,574

[22] Filed: Nov. 24, 1976

[51] Int. Cl.² .......................................... G01N 27/26
[52] U.S. Cl. ........................... 204/299 R; 204/180 G
[58] Field of Search ............... 204/180 G, 180 S, 299; 23/253 R, 230 B

[56] References Cited

U.S. PATENT DOCUMENTS

| | | | |
|---|---|---|---|
| 3,499,360 | 3/1970 | Davis | 204/180 G |
| 3,616,387 | 10/1971 | Siebert | 204/180 G |
| 3,622,484 | 11/1971 | Cawley | 204/180 G |
| 3,751,357 | 8/1973 | Rains | 204/180 G X |
| 3,879,280 | 4/1975 | Peterson et al. | 204/299 |
| 3,930,983 | 1/1971 | Sieber | 204/299 |
| 3,932,229 | 1/1976 | Grandine | 204/180 G |
| 3,932,265 | 1/1976 | Hoefer | 204/299 |

*Primary Examiner*—Arthur C. Prescott
*Attorney, Agent, or Firm*—Darrell G. Brekke; Armand McMillian; John R. Manning

[57] ABSTRACT

An apparatus for performing electrophoresis and a multiple-sample applicator for use therewith. Electrophoresis is a physical process in which electrically charged molecules and colloidal particles, upon the application of a DC current, migrate along a gel or a membrane that is wetted with an electrolyte. If a membrane is used, its middle section is kept in tension horizontally above an electrolyte tank, while the ends of the membrane hang down into the electrolyte. If a gel is used, it is held in a tray which is placed on a cooling plate, and wicks make contact with the electrolyte. The tank has unique protected electrodes for conducting the DC current.

A multiple-sample applicator is provided which coacts with a novel tank cover to permit an operator either to depress a single button, thus causing multiple samples to be deposited on the gel or on the membrane simultaneously, or to depress one or more sample applicators separately by means of a separate button for each applicator.

Greater resolution is achieved by performing two dimensional migrations in a square gel tray. First, the sample is pulled apart in a linear path by the electric current, and then the square gel tray is lifted and turned 90° so that the first migration is pulled apart from an orthogonal direction. The square gel tray is held in place at two opposite corners by retainers on the temperature-controlled plate. These retainers insure an exact 90° change when the tray is repositioned.

12 Claims, 18 Drawing Figures

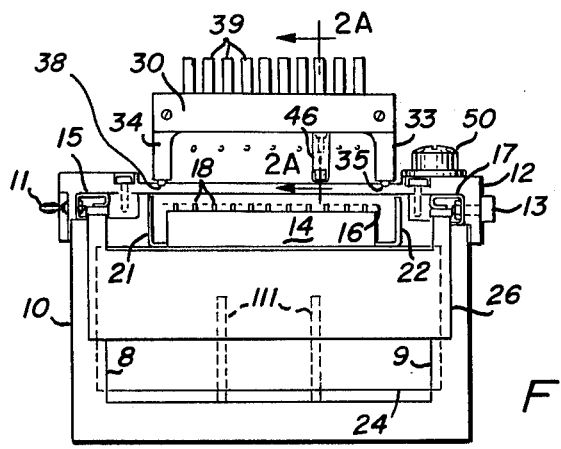
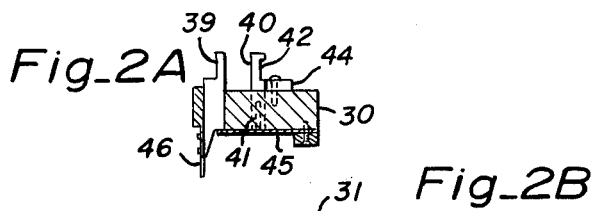
Fig_2A
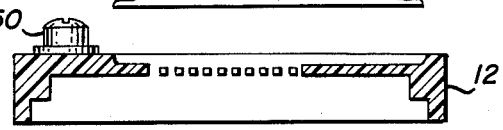
Fig_2B
Fig_1
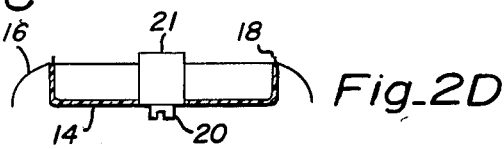
Fig_2C
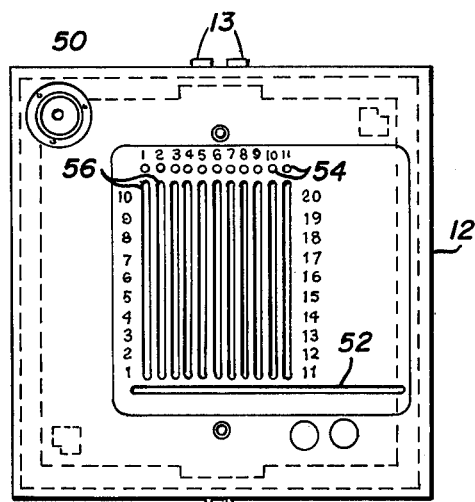
Fig_2E
Fig_3
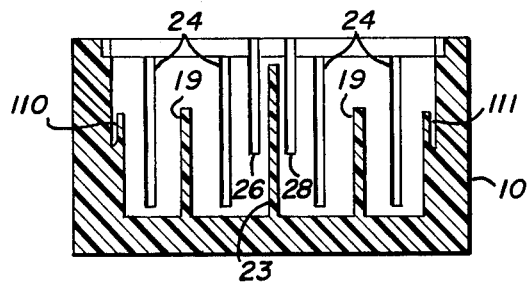
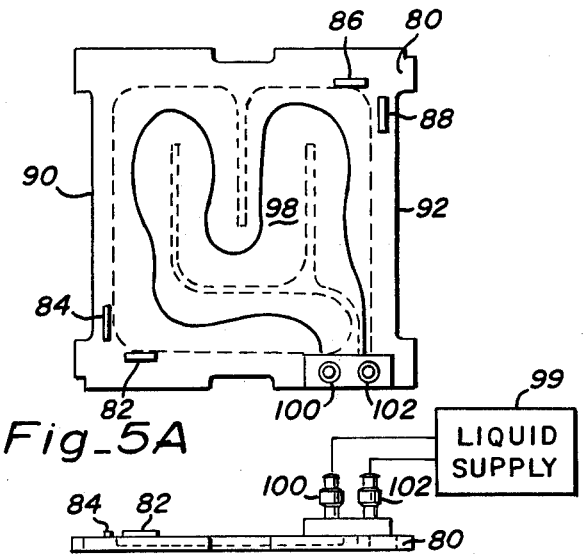
Fig_5A
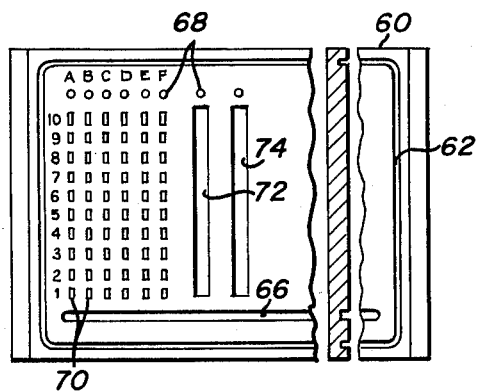
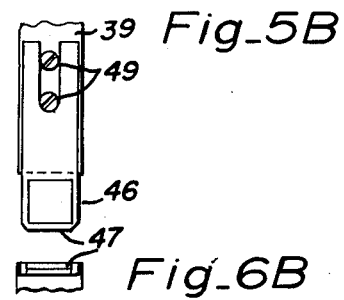
Fig_6A
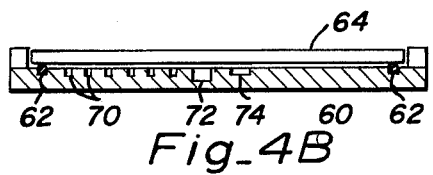
Fig_4B
Fig_5B
Fig_6B

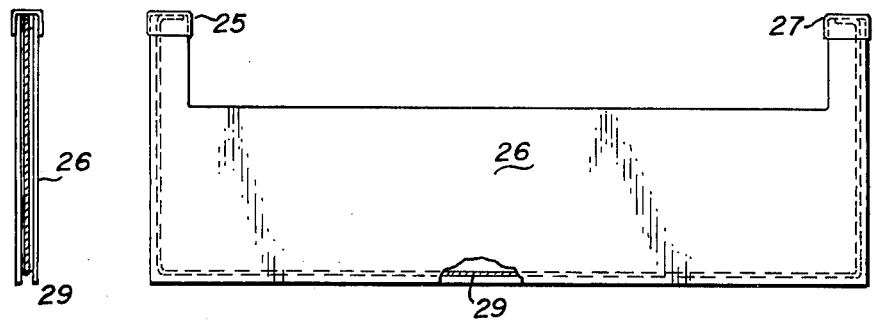
Fig._7B   Fig._7A
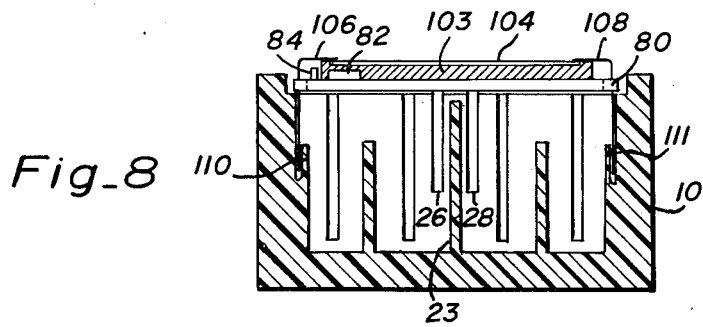
Fig._8
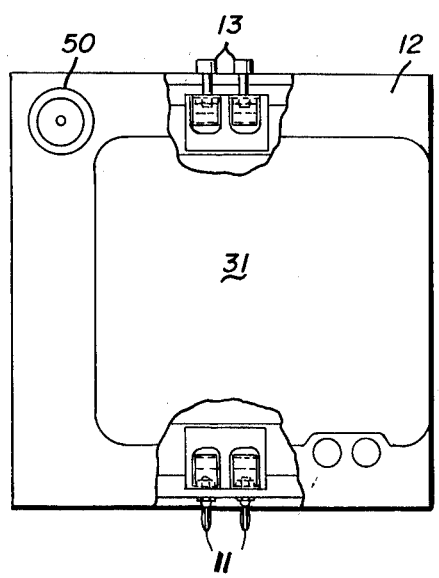
Fig._9
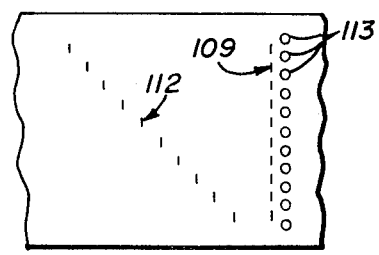
Fig._10

AUTOMATIC MULTIPLE-SAMPLE APPLICATOR AND ELECTROPHORESIS APPARATUS

The invention described herein was made in the performance of work under a NASA contract and is subject to the provisions of Section 305 of the National Aeronautics and Space Act of 1958, Public Law 85-568 (72 Stat. 435; 42 U.S.C. 2457).

BACKGROUND OF THE INVENTION

1. Field of the Invention

The invention relates to electrophoresis and, more particularly, to electrophoresis apparatus employing multiple-sample applicators for applying antiserum to a membrane or gel utilized as a media for the electrophoresis process.

2. Description of the Prior Art

Prior apparatus has been employed for electrophoresis utilizing cellulose acetate as the supporting medium to carry samples which are to be separated and analyzed by the electrophoresis process. In the prior apparatus, a controlled tensioning device is utilized to hold the membrane taut and parallel to the base of the unit without any support in the center of the membrane. This arrangement prevents pooling of liquid and retains a uniform moisture content in the membrane. The prior apparatus also provided an indexing device which operates semiautomatically to provide for the placing of eight samples, one at a time, on a number of fixed positions on the membrane. These eight samples are placed in a row in any one of three different positions relative to the cathode and anode of the apparatus and are electrophoresed simultaneously.

One disadvantage of the prior apparatus is that the applicator used to apply the samples to the membrane can only apply a single sample at a time. This is time-consuming and also the samples supplied first are subject to local diffusion and mobility due to convection currents during the time that subsequent samples are being applied. The drawback becomes critical when high resolution is necessary in comparative electrophoresis of unknown specimens.

An example of the existing state of the art of single-sample applicators is U.S. Pat. No. 3,317,418 which issued to Zec on May 2, 1967.

SUMMARY OF THE INVENTION

It is an object of the invention to provide an apparatus for the uniform and controlled transfer of multiple fluid samples onto a membrane in an electrophoresis apparatus.

Another object of the invention is to provide a one-piece membrane tensioning means in an electrophoresis apparatus which insures that the membrane is maintained in the desired taut relationship for coaction with a multiple-sample applicator.

Another object of the invention is to provide a novel electrolyte tank which can be utilized with either a square gel tray, permitting 90° rotation thereof, or a membrane tensioning means.

Another object of the invention is to provide an electrode assembly for use in an electrophoresis apparatus which provides a protected electrode with prevention of electrical feedthrough to the electrolyte tank.

The above objects are accomplished in accordance with the invention by providing an integrated multiple-sample applicator, electrolyte tank and cover, and multiple-sample holder. The multiple-sample applicator is adapted to pick up multiple specimens from corresponding wells in the sample holder as if they were one single sample. The sample applicator is provided with a central button which, when depressed, causes the applicator tips of a number of applicators to touch the surface of the fluid in the sample holder and fill by capillary action. The multiple-sample applicator is then placed on the electrolyte cell cover so that it fits in a predetermined slot or position relative to the electrodes. All of the multiple specimens are then transferred in one motion by depressing the central button. The applicator tips of the sample holders fall freely and independently onto the membrane or gel in the electrolyte tank. This feature of the invention has the advantage that it provides the best and most complete sample transfer. If the applicators were rigid, some of the samples might not transfer because of imperfections in the tautness of the membrane over its entire width.

In accordance with an aspect of the invention, any one of the applicators may be depressed independently of the others, such that increasing amounts of a given specimen can be deposited onto the same spot, such as might be required in the case of a very low solute concentration. Furthermore, each of the applicator tips can be readily replaced with tips of larger volume capacities, or tips can be inserted at alternate positions to allow longer sample application zones.

The sample applicators have the further advantage in that they eliminate the need for prior slot formation, as is usually required with gels. These applicators can cut through the gel and transfer all of the specimens in a single operation.

In accordance with a further aspect of the invention, a novel cell cover is provided with slots along the cover, such that samples can be placed in any of a number of fixed positions spaced at equal intervals between the cathode and the anode. This has the advantage that it is possible to electrophorese a number of samples at a time by selecting the appropriate slots along the cell cover. This utilization of space is not only economical and fast, it is also more accurate and reproducible in comparative electrophoresis.

In accordance with still a further aspect of the invention, a novel sample holder is provided which coacts with the multiple-sample applicator. The holder contains a number of rows containing wells corresponding to the number of multiple-sample applicators. Disposable capillaries are used to charge the wells with fresh samples. Prior to filling the wells, electrophoretic cells are set up containing the proper buffers needed for the determination of the desired constituents. Each cell is then properly labeled. The multiple-sample applicator is then utilized to pick up multiple individual specimens from the holder and transfer them simultaneously to the supporting membrane and at a predetermined position closer to either the negative or positive electrodes.

The foregoing and other objects, features and advantages of the invention will be apparent from the following more particular description of a preferred embodiment of the invention as illustrated in the accompanying drawings.

BRIEF DESCRIPTION OF THE DRAWINGS

FIG. 1 is a transverse sectional view taken along a line parallel to the dividing septum (23) of FIG. 2E;

FIGS. 2A–2E are an exploded cross-sectional elevation view of the electrophoresis apparatus of FIG. 1, showing in FIG. 2A the applicator assembly, FIG. 2B the plexiglass lid, FIG. 2C the intermediate cover, FIG. 2D the membrane holder, and FIG. 2E the tank;

FIG. 3 is a plan view of the cover shown in FIG. 2C;

FIGS. 4A and 4B are a plan view and side elevation, respectively, of a sample holder for use with the applicator assembly of FIG. 2A;

FIGS. 5A and 5B are a plan view and side elevation, respectively, of a temperature-controlled plate for use with the apparatus of FIGS. 1 and 2;

FIGS. 6A and 6B are a detail and end view, respectively, of the applicator tip shown in FIG. 2A;

FIGS. 7A and 7B are a front elevation and transverse sectional view, respectively, of one of the electrodes shown in FIG. 2E;

FIG. 8 is a front elevation of the tank of FIG. 2E with the temperature-controlled plate of FIG. 5A in place;

FIG. 9 is a plan view of the apparatus of FIG. 1, showing the electrical connection to the electrodes; and FIG. 10 is an illustration of various samples taken on a membrane in accordance with the apparatus of the present invention.

DESCRIPTION OF THE PREFERRED EMBODIMENT

Referring now to the drawings and most particularly to FIG. 1, an electrophoresis apparatus constructed in accordance with the principles of the invention is shown. The apparatus comprises a tank 10 which would contain an electrolyte solution. Within the tank are fixed baffles 19, removable baffles 24, septrum 23 and electrode frames 26, 28 which extend from slots in inner wall 8 to slots in inner wall 9. A membrane holder 14 is seated on septum 23 and two of the removable baffles 24. Channel 20 of membrane holder 14 straddles the top of septum 23. The membrane holder 14 is provided with tap grips 21, 22 and teeth 18. The teeth 18 engage perforations in a membrane 16 and keep the central portion of the membrane taut. The ends of membrane 16 are immersed in the electrolyte solution (not shown). The membrane must be made from a material that will "wick" the electrolyte solution to all areas of the membrane and keep the membrane saturated. Further, the membrane must have sufficient strength to withstand the force of the teeth when the membrane is wet. The membrane may, for example, be made from cellulose acetate, paper, or Cellogel. A cellulose acetate membrane can be kept and stored as a permanent record of the analysis. This is a very important factor in forensic science.

An applicator assembly 30 fits onto the cover 12. The applicator assembly is fitted with two feet 33, 34. The foot 34 has a registration pin 38 projecting from it, and the foot 33 has a runner bar 35 projecting from it. The pin 38 and runner 35 are adapted to fit into a runner bar slot and registration pinholes on either the coverplate of FIG. 3 or the sample holder of FIG. 4, which will be described subsequently.

The cover 12 includes male and female connectors 11, 13 which make contact with the electrode wire 29 through spring interlocks 15 and 17, respectively on the electrode frame 26. When the cover 12 is removed from the top of the tank 10, the electrical connection to the electrode wire 29 is broken by means of the spring interlocks. The electrode wire 29 is shown in more detail in FIGS. 7A and 7B. A platinum wire 29 is run around the slotted periphery of the electrode frame 26. The wire is connected to metal contacts 25 and 27, which complete a circuit to spring interlocks 15 and 17 shown in FIG. 1. As shown in FIG. 2E, two electrode frames 26 and 28 are placed in the tank 10 which has slots in its walls to receive the frames.

Referring now to FIG. 2A, the applicator assembly 30 will be described in more detail. The applicator assembly comprises a plurality of applicator button 39 which are adapted to hold an applicator shown in detail in FIG. 6.

The applicator buttons 39 are held in place by means of a plurality of leaf springs 45 which hold each button individually in place. A release button 40 is provided with a long arm 41 which extends across all of the parallel leaf springs 45. When the button 40 is depressed downward, all of the leaf springs are released such that all of the applicator buttons 39 are free to drop by force of gravity. The release button 40 is fitted with a groove 42, such that, when it is in the depressed position, a locking bar 44 is able to slide into the groove 42 and hold the release button in the lower position. When the applicator 30 is not in use, a protective plexiglass lid 31, FIG. 2B, is placed over the cover 12, FIG. 2C.

Referring to FIGS. 6A and 6B, the applicator tip 46 is shown in more detail. The applicator tip includes a capillary opening 47 for holding the sample fluid. The applicator tip 46 is held in place by two spring-loaded split pins 49, such that the tip is easily removed.

The applicator tip 46 may be modified in length or width; for example, to vary the amount of sample held, or to be wide enough to cover more than one applicator position.

Referring to FIG. 2D, the membrane holder 14 is shown in detail. The membrane holder is made of one piece of molded flexible plastic. The holder is fitted with teeth 18 and can be bent inwardly, such that the teeth 18 grip corresponding perforations in a membrane 16. When released, holder 14 applies tensile force to the membrane and maintains it taut. To avoid tearing the membrane, teeth 18 are preferably semicylindrical projections or cylindrical projections, and membrane perforations 113, FIG. 10, are circular.

Referring to FIG. 3, the intermediate cover 12 is shown in plan view. The cover includes a level 50 for visually leveling the entire apparatus. A cover runner bar slot 52 is provided to receive the runner bar 35 of the applicator assembly 30. The cover is also provided with cover registration pinholes 54 for receiving the registration pin 38 of the applicator assembly 30. Applicator slots 56 are provided in the cover 12, such that the applicator tips 46 are able to pass through the slot when the applicator buttons 39 are depressed, either individually or jointly by means of the release button 40.

It can now be seen from FIG. 3 that the ten parallel applicator tips 46, illustrated in FIG. 1, can pass through one of the slots 56 depending upon which slot is chosen by means of placing the registration pin 38 on the applicator assembly 30 into one of the pinholes 54.

Referring now to FIGS. 4A and 4B, a sample holder 60 is shown. The sample holder 60 is provided with a rubber gasket 62 placed in a groove, which gasket is adapted to seal a plexiglass plate cover 64 which can be placed over the sample holder. The holder is provided with a runner bar slot 66 and registration pinholes 68. These are adapted to receive the registration pin 38 and the runner bar 35 of the applicator assembly 30 in a manner similar to that described above with respect to the cover 12.

The sample holder 60 is provided with a plurality of sample pits 70 in rows corresponding to the pinholes (A-F). Each row contains 10 pits, such that each of the applicator tips 46, shown in FIG. 1, is able to enter a corresponding pit.

The sample holder is also provided with a rinse trough 72 and a blotter trough 74, and corresponding registration holes, such that, when the registration pin 38 of the applicator assembly 30 is placed in the corresponding hole, the applicators may be rinsed in the trough 72 by depressing the release button and may be blotted in the blotter trough 74 in a similar manner.

Referring now to FIGS. 5A and 5B, the temperature-controlled plate 80 will be described in more detail. The temperature-controlled plate is utilized with a gel medium is desired rather than a membrane. Plate 80 is substituted for membrane holder 14. The temperature-controlled plate is fitted with retainers 82, 84, 86, 88 for receiving and holding in place a square tray containing a gel material. For example, in the detection of lipoprotein (Lp), an agarose gel may be employed. Electrical contact between the gel and the electrolyte solution is made by means of a moist wick and, therefore, wick recesses 90, 92 are provided in the temperature-controlled plate. A temperature-controlled liquid is pumped from supply 99 into plate inlet 100. After the liquid passes through plate channel 98, it leaves via outlet 102 and returns to supply 99.

Referring now to FIG. 8, the temperature-controlled plate 80 is shown in place within the tank 10. A square tray 103 holding a gel 104 is placed on plate 80 and is kept in fixed position by retainers 82, 84. Tray 103 is preferably made from a material that is an electrical insulator and a good thermal conductor. Additionally, the tray must be inert to the electrolyte. As the plate is adapted to receive a square tray, 90° rotation of the gel media is possible. Greater resolution is obtained by performing two migrations on the gel 104. First, the sample is pulled apart in a linear path by the electric current. The gel tray is then rotated 90° and the first migration is pulled apart from an orthogonal direction.

Contact with the electrolyte solution is made by means of wicks 106, 108 which rest on the edge of the gel and pass down through wick recesses 90, 92, FIG. 5A, and into the electrolyte solution. The tank 10 is provided with wick-retaining members 110 and 111 for receiving the lower end of each wick and holding the ends in place within the electrolyte solution. The wick-retaining members prevent the wicks from sliding off the gel and align the wicks so that they contact the gel 104 evenly across the surface. The wick alignment prevents a contact gradient from occurring. Wicks 106, 108 may be made, for example, from filter paper or plastic sponge.

During the electrophoresis process, the electric current flowing through the gel 104 causes heat to be dissipated in the gel. The thermal convection in the gel tends to broaden the bands and cause errors. This band broadening is alleviated by passing a liquid through plate 80 which has a temperature less than the ambient temperature. For some measurements, for example, a plate temperature of 4° C has been found to be suitable. In the isoenzyme detection process it is common to heat the gel to approximately 37° C after the electrophoresis current is turned off and chemicals are added to the gel that will interact with only the specific enzyme that is sought. The instant invention permits the entire isoenzyme detection process to occur while the gel tray remains on plate 80. During the electrophoresis migration step a liquid with a lower-than-ambient temperature is passed through plate 80. Later, after the electricity is removed, a higher-than-ambient temperature liquid is passed through plate 80 to enhance the detection of the desired enzyme.

Referring to FIG. 9, a top view of the cover 12, shown in FIG. 3, is shown with cutaways illustrating the male and female connectors 11, 13. It can be seen from this drawing that similar apparatus can be electrically connected together by inserting the plugs 11 of one apparatus into the jacks 13 of an adjacent apparatus.

In FIG. 10, pattern 109 shows the configuration of the samples on membrane 16 when they are simultaneously applied. Pattern 112 depicts how the samples will be oriented if the applicator is indexed after successive applicator button is depressed. Perforations 113 in the membrane are engaged by teeth 18 in the membrane holder 14.

SUMMARY

What has been described is a multiple-sample applicator, a novel cell cover assembly, a novel sample holder, a novel bridge assembly to hold a cellulose acetate membrane taut at controlled tension, and a novel temperature-controlled plate for holding a gel tray and a novel holder and guide for electrolyte wicks.

The multiple-sample applicator is adapted to pick up multiple specimens from corresponding pits, or wells, in a specimen sample holder adapted to receive the multiple applicators. When a release button is depressed, all of the applicator tips are lowered by gravity into respective pits to touch the surface of the fluid of the sample and fill by capillary action. The applicator is then placed on the specially-designed cell cover, so that it fits a predetermined slot position relative to the electrode. Depressing the release button transfers all of the multiple specimens in one motion. This is accomplished by releasing springs which hold the applicators, such that the applicators are free to fall independently onto the cellulose acetate membrane. Should it be necessary to apply increasing amounts of a given specimen onto the same spot on the membrane, such as in the case of a very low solute concentration, then any one or all of the sample applicators can be actuated separately. The applicator tips are designed to be easily removed and thus can be readily replaced with tips of larger volume capacities, or tips can be inserted at alternate positions to allow longer sample application zones.

The same multiple-sample applicator is utilized with gel as a supporting medium. No prior slot formation in the gel is required, because the applicators are designed to cut through the gel and transfer all of the specimens in a single operation.

A novel cell cover has been disclosed which permits placing samples in any of a number of fixed positions spaced at equal intervals between the cathode and anode. This allows flexibility in the placement of the sample on the supporting medium relative to the cathode and anode, so as to effect and determine the degree of separation and resolution of the individual components being analyzed.

A novel sample holder is disclosed which is fitted with registration means to receive the multiple-sample applicator. Several rows of pits are provided for holding multiple samples, such that by choosing a particular registration pinhole on the holder any one of the rows can be selected and corresponding multiple samples can be transferred simultaneously by depressing the single release button on the multiple-sample applicator assembly. The sample holder is also provided with a rinse trough and a blotter trough which permits rinsing and blotting of all of the applicators simultaneously by depressing a single release button.

While the invention has been particularly shown and described with reference to a preferred embodiment thereof, it will be understood by those skilled in the art that various changes in form and details may be made therein without departing from the spirit and scope of the invention.

What is claimed is:

1. An electrophoresis tank, comprising:
   means for holding a sample-supporting medium;
   a multiple-sample applicator means, including individually operable multiple-sample applicators having tips for holding fluid samples to be analyzed;
   a cover for said tank adapted to receive said applicator tips through corresponding openings therein; and
   means coacting with said multiple-sample applicators for releasing said applicators simultaneously, to thereby permit said applicators to fall by force of gravity into said tank to thereby contact said sample-supporting medium.

2. The combination, according to claim 1, wherein said multiple-sample applicator means further includes multiple spring-retaining means adapted to keep each of said multiple-sample applicators under spring tension in a retracted position.

3. The combination, in accordance with claim 2, wherein said multiple-sample applicator means further includes at least one release button which is adapted to coact with a plurality of said spring-retaining means, such that, when said release button is depressed, the tension on all of said springs is released simultaneously to thereby release said applicators simultaneously.

4. The combination, in accordance with claim 3, wherein said multiple-sample applicators are each adapted to be depressed individually, to thereby depress the individual spring-retaining means retaining said applicator, to thereby bring the applicator tip into contact with said supporting medium.

5. The combination, in accordance with claim 1, wherein said cover has a number of slots cut therein adapted to receive said multiple-sample applicator tips, and further comprises registration pinholes for receiving a registration pin located on said multiple-sample applicator to thereby register said multiple-sample applicator tips with a slot corresponding to one of said registration pinholes.

6. The combination, in accordance with claim 1, further comprising a sample holder, including a plurality of rows of sample pits adapted to hold fluid, and a number of registration holes corresponding to each row and adapted to coact with a corresponding pin on said multiple-sample applicator, whereby said multiple-sample applicator can be placed in registration with one of said rows to thereby permit the simultaneous transfer of fluid in said pits to said applicator tips.

7. The combination, in accordance with claim 6, wherein said sample holder further comprises a rinse trough and a corresponding rinse trough registration hole whereby said multiple-sample applicators can be rinsed in a fluid in said rinse trough by aligning said registration pin on said applicator with the registration hole corresponding to said rinse trough.

8. The combination, in accordance with claim 7, wherein said sample holder further comprises a blotter trough and a corresponding blotter trough registration hole whereby said multiple-sample applicators can be blotted subsequent to being rinsed in a fluid in said rinse trough by aligning the registration pin on said applicator with the registration hole corresponding to said blotter trough.

9. The combination, according to claim 1, wherein said means for holding a sample-supporting medium comprises a one-piece, substantially U-shaped resilient member having protruding teeth adapted to engage perforations in said medium, when said holding means is depressed and said teeth are brought into engaging contact with said perforations.

10. The combination, according to claim 1, wherein said means for holding a sample-supporting medium comprises a temperature-controlled plate having a flat surface for supporting a square-shaped tray containing a sample-supporting medium, with retaining means for holding said tray in a first position, and in an alternate position which is orthogonal to said first position.

11. The combination, according to claim 10, wherein said tank further comprises retaining means on the inner sides of said tank for holding one end of a wick adapted to contact said medium at another end of said wick and an electrolyte in said tank at said one end of said wick, such that said wick is maintained in a fixed position with respect to said medium.

12. The combination, according to claim 1, wherein said cover further includes: first, electrical connectors adapted to receive mating connectors from an external electrical power source; and second, electrical connectors adapted to receive mating connectors on another tank placed side-by-side with said electrophoresis tank.

* * * * *